(12) United States Patent
Bahadir et al.

(10) Patent No.: US 11,510,703 B2
(45) Date of Patent: Nov. 29, 2022

(54) EXTERNAL FIXATOR

(71) Applicant: Yeditepe Universitesi, Istanbul (TR)

(72) Inventors: Tugcenur Bahadir, Samsun (TR); Alper Yaman, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 424 days.

(21) Appl. No.: 16/466,017

(22) PCT Filed: Jun. 8, 2017

(86) PCT No.: PCT/TR2017/050256
§ 371 (c)(1),
(2) Date: Jun. 1, 2019

(87) PCT Pub. No.: WO2018/101896
PCT Pub. Date: Jun. 7, 2018

(65) Prior Publication Data
US 2021/0220016 A1    Jul. 22, 2021

(30) Foreign Application Priority Data

Dec. 1, 2016  (TR) .................................. 2016/17639

(51) Int. Cl.
*A61B 17/62*    (2006.01)
(52) U.S. Cl.
CPC .................................... *A61B 17/62* (2013.01)
(58) Field of Classification Search
CPC ..... A61B 17/62; A61B 17/64; A61B 17/6441; A61B 17/645; A61B 17/66; Y10T 403/33; Y10T 403/4628; Y10T 403/4631; Y10T 403/4674; Y10T 403/4682
See application file for complete search history.

(56) References Cited

U.S. PATENT DOCUMENTS

| | | | | |
|---|---|---|---|---|
| 2,926,382 A | * | 3/1960 | Knese ...................... | E05D 7/10 16/261 |
| 3,805,325 A | * | 4/1974 | Lee ......................... | E05C 19/08 16/262 |
| 3,855,895 A | * | 12/1974 | Francis, Jr. ............. | F16B 2/248 411/337 |
| 4,235,560 A | * | 11/1980 | Schimmel ............. | E04G 17/042 403/388 |
| 5,062,844 A | | 11/1991 | Jamison et al. | |
| 5,275,598 A | | 1/1994 | Cook | |

(Continued)

FOREIGN PATENT DOCUMENTS

| | | |
|---|---|---|
| BR | 8502309 U | 9/2007 |
| GB | 1472097 A | 4/1977 |
| SU | 1688862 A1 | 11/1991 |

*Primary Examiner* — Eduardo C Robert
*Assistant Examiner* — Tara Rose E Carter
(74) *Attorney, Agent, or Firm* — Bayramoglu Law Offices LLC

(57) ABSTRACT

An external fixator utilized in orthopedic surgeries such as the repair of segmental fractures, correction of congenital or development deformities, and limb lengthening. The external fixator is comprised of half rings that utilize connectors to form full rings, threaded rods that fit into rod holes, channel slots, wires that pass through bone and soft tissue, and fixation bolts that can be positioned with minimal effort by a surgeon, minimal pain to a patient, and minimal risk of infection.

1 Claim, 3 Drawing Sheets

(56) References Cited

U.S. PATENT DOCUMENTS

| | | | | |
|---|---|---|---|---|
| 5,469,319 A * | 11/1995 | Takeda | ............ | G11B 23/08757 |
| | | | | 242/346 |
| 5,496,319 A * | 3/1996 | Allard | ................ | A61B 17/6441 |
| | | | | 606/56 |
| 7,226,449 B2 * | 6/2007 | Venturini | ............... | A61B 17/62 |
| | | | | 606/56 |
| 2004/0073212 A1 * | 4/2004 | Kim | ...................... | A61B 17/62 |
| | | | | 606/56 |
| 2008/0300606 A1 * | 12/2008 | Moorcroft | .............. | A61B 17/62 |
| | | | | 606/103 |

\* cited by examiner

EXTERNAL FIXATOR

CROSS REFERENCE TO THE RELATED APPLICATIONS

This application is the national phase entry of International Application No. PCT/TR2017/050256, filed on Jun. 8, 2017, which is based upon and claims priority to Turkish Patent Application No. 2016/17639, filed on Dec. 1, 2016, the entire contents of which are incorporated herein by reference.

TECHNICAL FIELD

The present invention relates to an ILIZAROV™ external fixator which is used in orthopedic surgeries such as repair of segmental fractures, correction of congenital or developmental deformities, and limb lengthening.

BACKGROUND

External fixators are used in orthopedics to stabilize and align bones and soft tissues. The ILIZAROV™ external fixator stabilizes limbs by passing the KIRSCHNER™ wires, which are fixed to an external frame, typically a ring, through bones transversely, fixing them in place.

In the ILIZAROV™ external fixator, each set of half rings is placed around the site needed to be stabilized, and then assembled into a full ring. The threaded rods are passed through the holes at regular intervals on the rings and secured by means of nuts from the bottom and the top of the rings. Thus a cage like structure is formed along the limb by the rings and the rods. To adjust the position of the rings relative to each other, the nuts are loosened and the rings moved along the axis of the threaded rods. After establishing the desired position of the rings, the nuts are retightened. The wires which are passed through tissues and bone are fixed to the rings via wire fixation bolts.

In currently existing ILIZAROV™ external fixators, there is a large amount of discomfort and pain subjected on the patient as well as difficulty in mounting the fixture due to the form of engagement of the rods to the rings. Besides bending over the wires may also pose a risk of infection for both the surgeon and the patient.

It is therefore necessary to develop an external fixator which minimizes the amount of pain and discomfort a patient is subjected to and can be more easily applied by a surgeon.

United States patent document no. U.S. Pat. No. 7,226,449B2, another application known in the state of the art, discloses an ILIZAROV™ external fixator used in orthopedic treatments. The rods of the external fixator are comprised of two parts connected by a mechanism in order to easily adjust the distance between the rings.

SUMMARY

The objective of the present invention is to provide an external fixator which is used for repairing segmental fractures, bone infections, correcting congenital or developmental deformities, and limb lengthening.

The objective of the present invention is to provide an external fixator wherein the rings and rods can be positioned with minimal effort by a surgeon and minimal pain and discomfort to a patient.

The objective of the present invention is to provide an external fixator wherein the rings and rods can be positioned with minimal effort by a surgeon and minimal pain and discomfort to a patient.

The objective of the present invention is to provide an external fixator wherein the KIRSCHNER™ wires can be bent over safely to minimize the risk of infection.

BRIEF DESCRIPTION OF THE DRAWINGS

An external fixator developed to fulfill the objective of the present invention is illustrated in the accompanying figures wherein.

Figure 1:
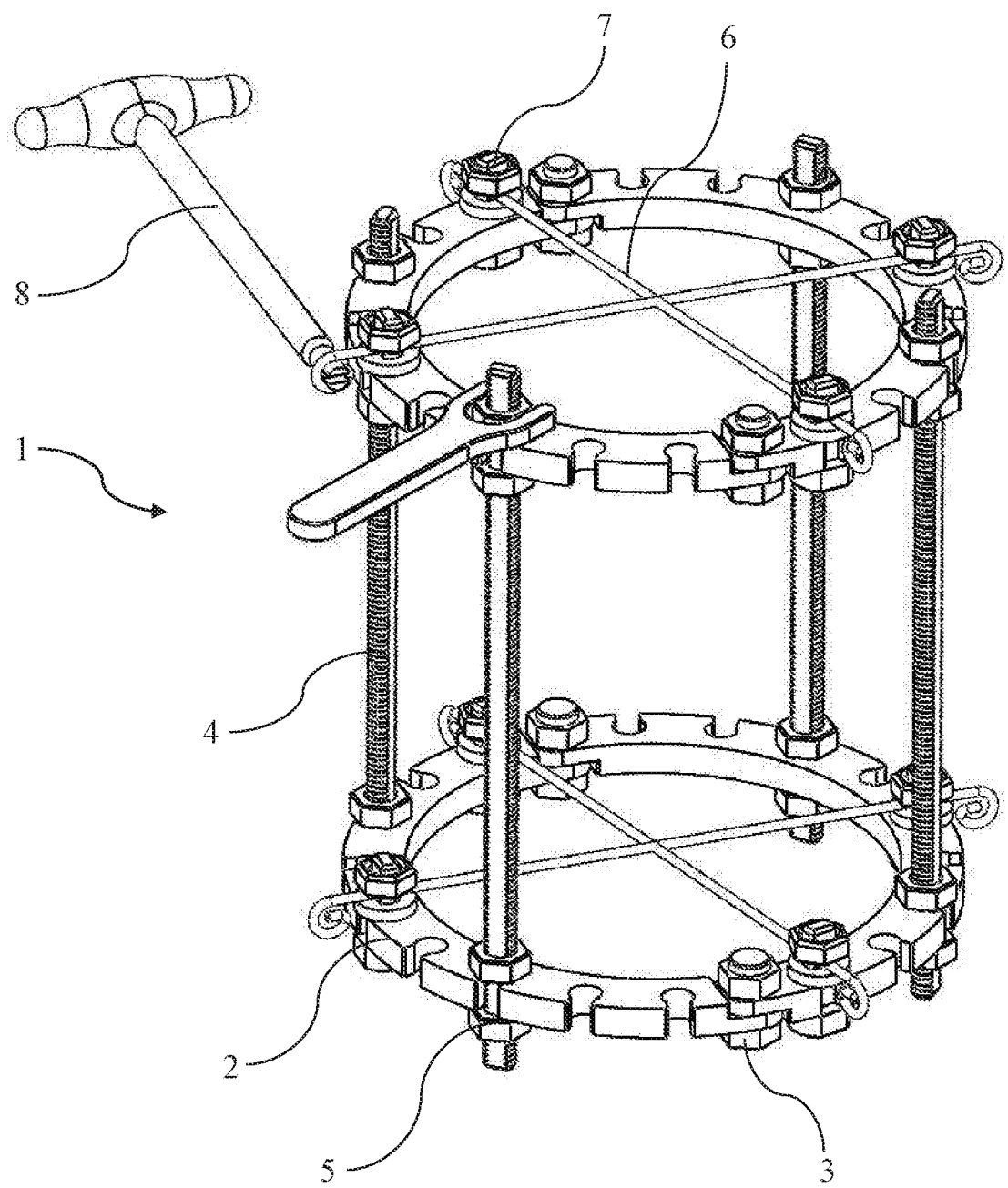
FIG. 1 is a perspective view of the external fixator.
Figure 2:
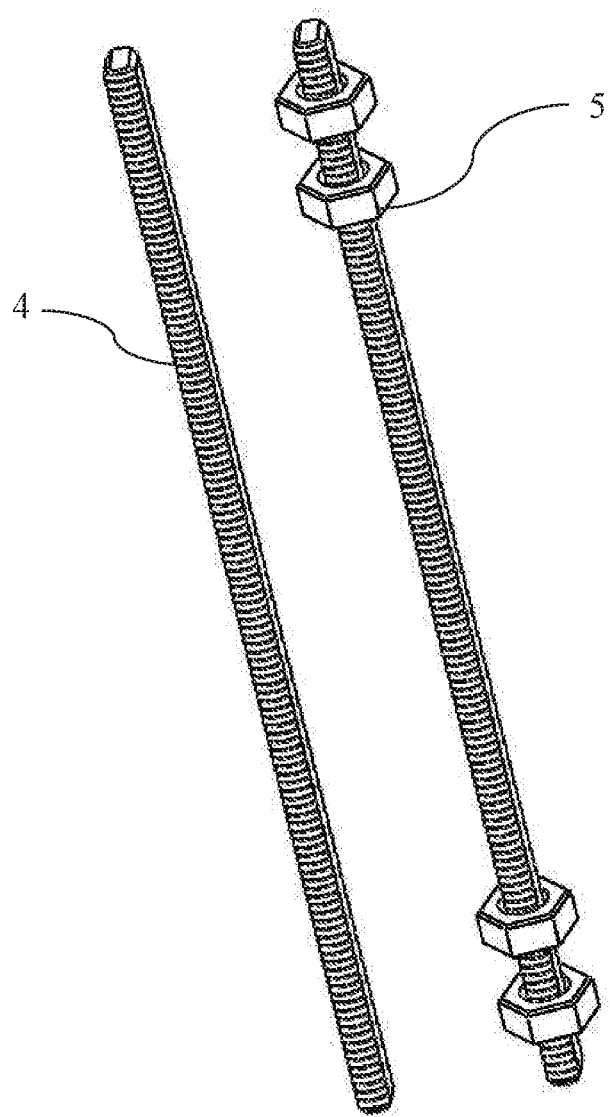
FIG. 2 is a perspective view of the rods.
Figure 3:
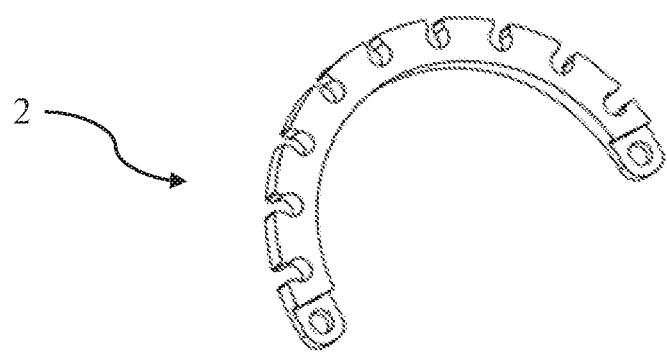
FIG. 3 is a perspective view of the half ring.
Figure 4:
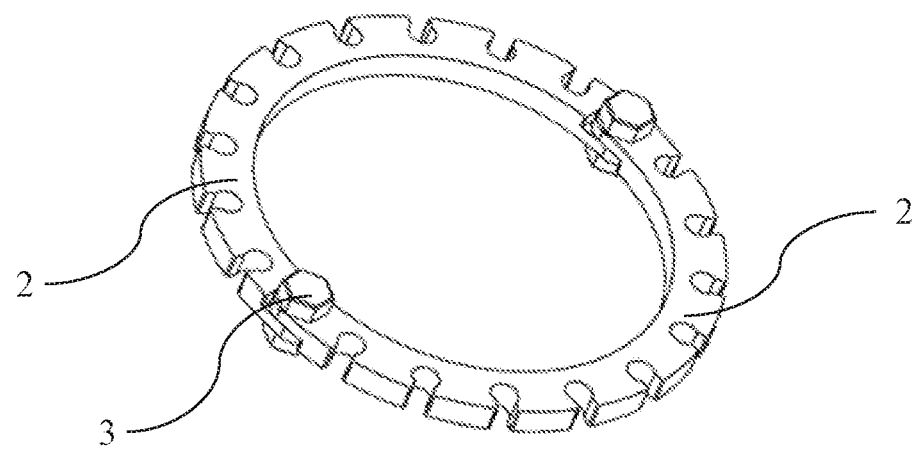
FIG. 4 is a perspective view of connected half rings.

The components shown in the figures are each given reference numbers as follows:
1. External fixator
2. Half ring
3. Connector
4. Rod
5. Nut
6. KIRSCHNER™ wire
7. Wire fixation bolt
8. Apparatus

DETAILED DESCRIPTION OF THE EMBODIMENTS

An external fixator (1) used in orthopedics comprises
at least four half rings (2) which have ledged areas on each end that provide connections to form full rings wherein each half ring comprises rod holes at certain intervals parallel to the axis of the ring, and channel slots between the rod holes and outer edge of the ring wherein the channel slots are narrower than the rod holes,
at least four connectors (bolts and nuts)(3) which fix the half rings to each other through the connection holes located on the ledges areas of the half rings (2),
at least three threaded rods (4), which have the same diameter with those of the rod holes and fit into the rod holes, and which are in the form of bars that are trimmed longitudinally from two opposite sides of the diameter so as to be equal to the width of the channel slots,
nuts (5) which fix the rods (4) to the half rings (2),
at least one KIRSCHNER™ wire (6) to fix the bones and soft tissues,
at least two wire fixation bolts (7) which are passed through the rod holes to fix the KIRSCHNER™ wire (6) at both ends to the half rings (2).

The half rings (2) form two full rings that are aligned approximately to proximodistal axis at the bottom and the top as such in an external fixator (1), which is to encircle the site needed to be stabilized. Each rod (4) is fitted into the rod hole by passing through the channel slot, and after being rotated 90 degrees, it is ensured that it will not get dislocated from the channel slot and is fixed to the half rings (2) via the nuts (5). Distance between the rings can be adjusted by loosening the nuts (4).

The KIRSCHNER™ wire (6), which is passed through the bones and soft tissues, is fixed by wire fixation bolts (7)

from both ends thereof and connected to the rings. The sharp ends of the KIRSCHNER™ wire (6) are usually bent over to avoid injury.

In a preferred embodiment of the invention, to bend the ends of the KIRSCHNER™ wire (6), an apparatus (8) is used, whose one end holds the wire and the other end has a handle to easily bend. This way, inward/outward migration of the wire are prevented and both the surgeon and the patient are protected from injury.

What is claimed is:

1. An external fixator used in orthopedics, comprising:
   at least one wire to stabilize bones and soft tissues;
   at least four half rings having ledged areas on each end which provide connections to form full rings and rod holes at intervals parallel to an axis of each half ring,
   at least four connectors to fix the at least four half rings to each other through connection holes,
   a channel slot is provided between the rod holes and an outer edge of each half ring, wherein, the channel slot is narrower than the rod holes,
   at least three threaded rods, wherein each threaded rod has a same diameter as that of the rod holes and fits into the rod holes, and each threaded rod is trimmed longitudinally throughout the rod from two opposite sides of the diameter and have each side equal to a width of the channel slot,
   nuts to fix the at least three threaded rods to the at least four half rings,
   at least two wire fixation bolts passing through the rod holes to fix the at least one wire at both ends to the at least four half rings, and
   an apparatus to bend ends of the at least one wire, wherein a first end of the apparatus holds the at least one wire and a second end of the apparatus comprises a handle for bending the ends of the at least one wire, wherein the at least one wire extends out from the at least two wire fixation bolts for the first end of the apparatus to hold to the at least one wire.

\* \* \* \* \*